United States Patent [19]
Grass

[11] Patent Number: 6,146,883
[45] Date of Patent: Nov. 14, 2000

[54] PACKING DEVICE FOR TRANSPORTING CONFLUENT CELL MONOLAYERS

[75] Inventor: George M. Grass, Tahoe City, Calif.

[73] Assignee: Navicyte, Inc., San Diego, Calif.

[21] Appl. No.: 09/320,512

[22] Filed: May 26, 1999

Related U.S. Application Data

[60] Provisional application No. 60/100,342, Sep. 14, 1998.
[51] Int. Cl.$^7$ ..................................................... C12M 3/00
[52] U.S. Cl. .................................... 435/307.1; 435/288.4; 435/297.5; 435/305.3
[58] Field of Search .............................. 435/288.4, 297.1, 435/297.5, 305.3, 307.1

[56] References Cited

U.S. PATENT DOCUMENTS

| | | | |
|---|---|---|---|
| 3,186,917 | 6/1965 | Gerhardt et al. | 195/1 |
| 3,386,912 | 6/1968 | Lazare | 210/22 |

(List continued on next page.)

FOREIGN PATENT DOCUMENTS

| | | | |
|---|---|---|---|
| 197 25 602A1 | 6/1997 | Germany | C12M 3/04 |
| 55-33362 | 8/1980 | Japan | B01D 13/00 |

OTHER PUBLICATIONS

Cheryan et al., "Membrane Bioreactors", *Membrane Separations in BiotechnologyMembrane Separations in Biotechnology*, (1986) pp. 284–300, published by Marcel Dekker, Inc., New York, New York.

Grass et al., "In Vitro Measurement of Gastrointestinal Tissue Permeability Using a New Diffusion Cell", *Pharmaceutical Research*, (1988) vol. 5, No. 6, pp 372 376.

Minuth et al., "Approach to an Organo–Typical Environment for Cultured Cells and Tissues", *BioTechniques* (1996) vol. 20, No. 3, pp. 498–501.

Minuth et al., "Construction of an Apparatus for Perfusion Cell Cultures Which Enables In Vitro Experiments Under Organotypic Conditions", *European Journal of Cell Biology* (1992) vol. 57, No. 1, pp. 132–137.

Perantoni et al., "Properties of Wilms' Tumor Line (TuWi) and Pig Kidney Line (LLC–PK$_1$) Typical of Normal Kidney Tubular Epithelium", In Vitro (1979) vol. 15, No. 6, pp. 446–454.

(List continued on next page.)

*Primary Examiner*—David A. Redding
*Attorney, Agent, or Firm*—Cooley Godward LLP

[57] ABSTRACT

A disposable or recyclable device is provided for packaging and transporting ready-to-use viable cell monolayers, particularly confluent cell monolayers. The device includes a liquid impervious housing having a housing base defining an interior filled with fluid medium, a plurality of detachable and spatially separated permeable membrane inserts each having a confluent cell monolayer attached thereon, and a removable lid. The permeable membrane inserts are disposed in an interior of the housing in a spatially addressable array and the housing base is sealed by the lid so as to separate the membrane inserts from an external environment and to exclude excess air from the fluid filled interior. The device optionally includes a disposable or recyclable environmental control system for regulating chemical and/or physical conditions during transport. Cell monolayers of the device are protected from mechanical injury so that assays or other experiments requiring even growth and dense cell populations can be performed upon delivery. The device of the invention also can be utilized for packaging and transporting multiple different types of cell monolayers on a variety of solid and microporous substrata, the cells normalized to any desired stage of cell cycle and/or growth, without the need to recalibrate cell cycle or synchronize growth upon receipt.

18 Claims, 14 Drawing Sheets

U.S. PATENT DOCUMENTS

| | | | |
|---|---|---|---|
| 3,508,656 | 4/1970 | Serfass et al. | 210/90 |
| 3,520,803 | 7/1970 | Iaconelli | 210/23 |
| 3,590,634 | 7/1971 | Pasternak et al. | 73/159 |
| 3,684,097 | 8/1972 | Mathewson, Jr. et al. | 210/321 |
| 3,904,480 | 9/1975 | Hull et al. | 195/66 B |
| 3,963,613 | 6/1976 | Chibata et al. | 210/195 R |
| 4,087,327 | 5/1978 | Feder et al. | 195/1.7 |
| 4,143,765 | 3/1979 | Moss, III | 206/445 |
| 4,212,742 | 7/1980 | Solomon et al. | 210/247 |
| 4,293,399 | 10/1981 | Belanger et al. | 204/195 P |
| 4,395,492 | 7/1983 | Rees | 435/283 |
| 4,446,229 | 5/1984 | Indech | 435/1 |
| 4,508,819 | 4/1985 | Rose | 435/1 |
| 4,537,860 | 8/1985 | Tolbert et al. | 435/240 |
| 4,661,458 | 4/1987 | Berry et al. | 435/284 |
| 4,666,853 | 5/1987 | Meserol et al. | 435/290 |
| 4,667,504 | 5/1987 | Hobson | 73/38 |
| 4,686,190 | 8/1987 | Cramer et al. | 435/291 |
| 4,734,372 | 3/1988 | Rotman | 435/291 |
| 4,734,373 | 3/1988 | Bartal | 435/296 |
| 4,852,389 | 8/1989 | Mayer et al. | 73/38 |
| 4,938,931 | 7/1990 | Cussler | 422/211 |
| 5,026,649 | 6/1991 | Lyman et al. | 435/284 |
| 5,084,393 | 1/1992 | Rogalsky | 435/284 |
| 5,139,951 | 8/1992 | Butz et al. | 435/284 |
| 5,141,873 | 8/1992 | Steudle et al. | 436/148 |
| 5,160,604 | 11/1992 | Nakamura et al. | 210/85 |
| 5,183,760 | 2/1993 | Sweetana et al. | 435/285 |
| 5,190,878 | 3/1993 | Wilhelm | 435/285 |
| 5,228,569 | 7/1993 | House | 206/372 |
| 5,415,277 | 5/1995 | Bernsten | 206/144 |
| 5,466,602 | 11/1995 | Lyman et al. | 435/297.1 |
| 5,693,537 | 12/1997 | Wilson et al. | 435/401 |
| 5,759,851 | 6/1998 | Mathus | 435/297.1 |
| 5,882,922 | 3/1999 | Tyndorf et al. | 435/305.3 |

OTHER PUBLICATIONS

Schinkel et al., "Absence of the mdrla P–Glycoprotein in Mice Affects Tissue Distribution and Pharmacokinetics of Dexamethasone, Digoxin, and Cyclosporin A", *J. Clin. Invest.* (1995) vol. 96, pp. 1698–1705.

Schoenwald et al., "Corneal Penetration Behavior of a β–Blocking Agents I: Physicochemical Factors", *Journal of Pharmaceutical Sciences* (1983) vol. 72, No. 11, pp. 1256–1281.

Ussing et al., "Active Transport of Sodium as the Source of Electric Current in the Short–Circuited Isolated Frog Skin", *Acta Phys. Scandinav.* (1950) vol. 23, pp. 110–127.

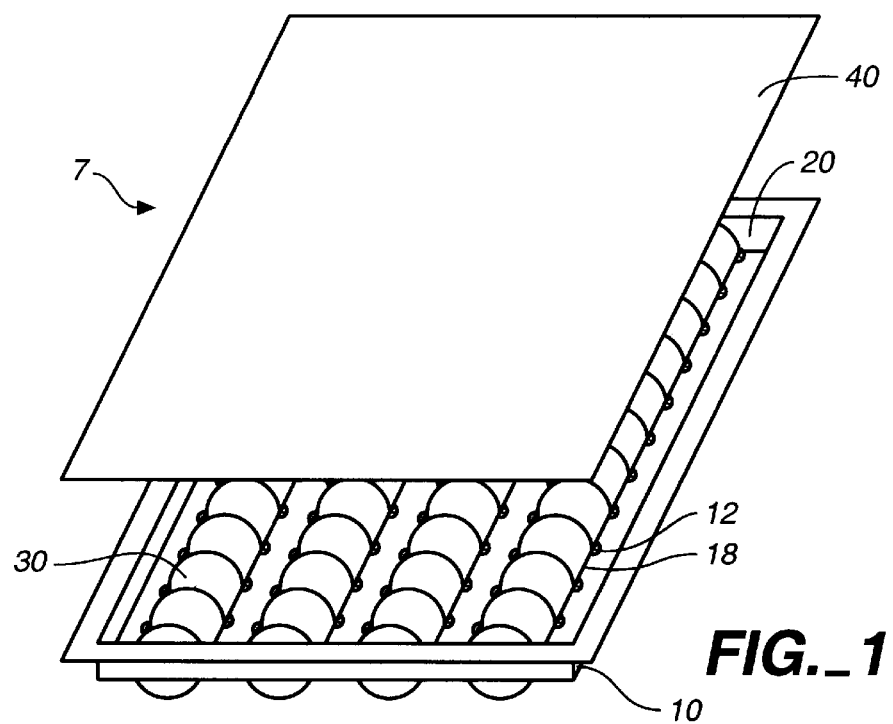
FIG._1
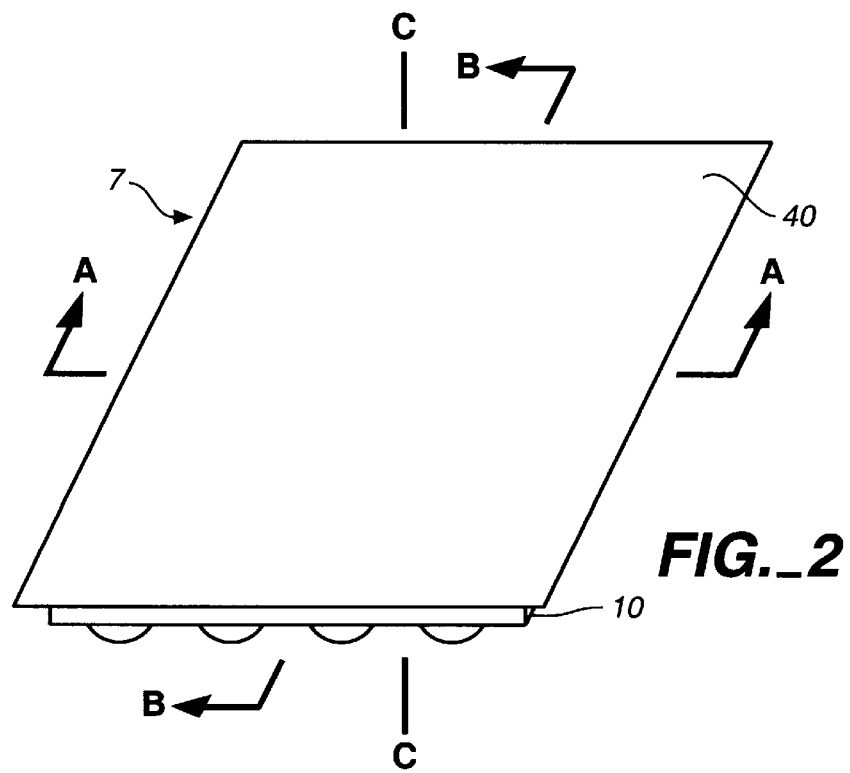
FIG._2

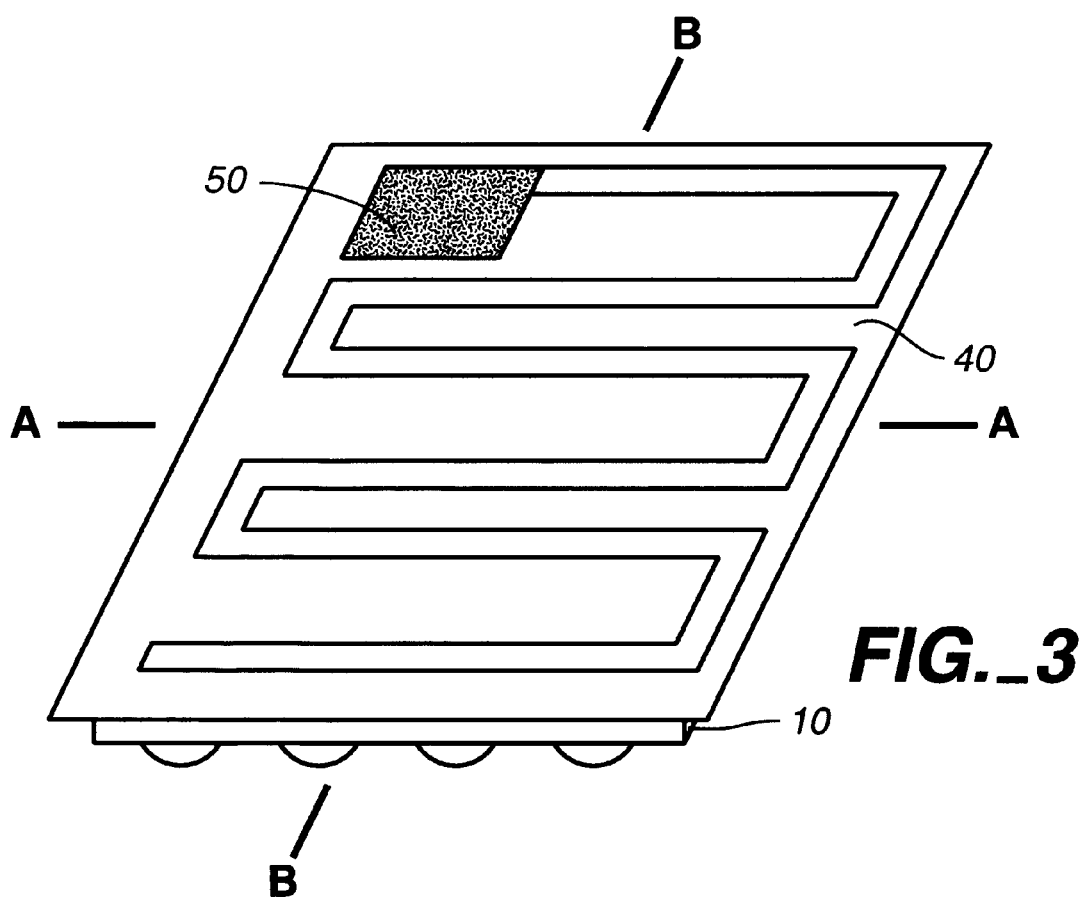
FIG._3

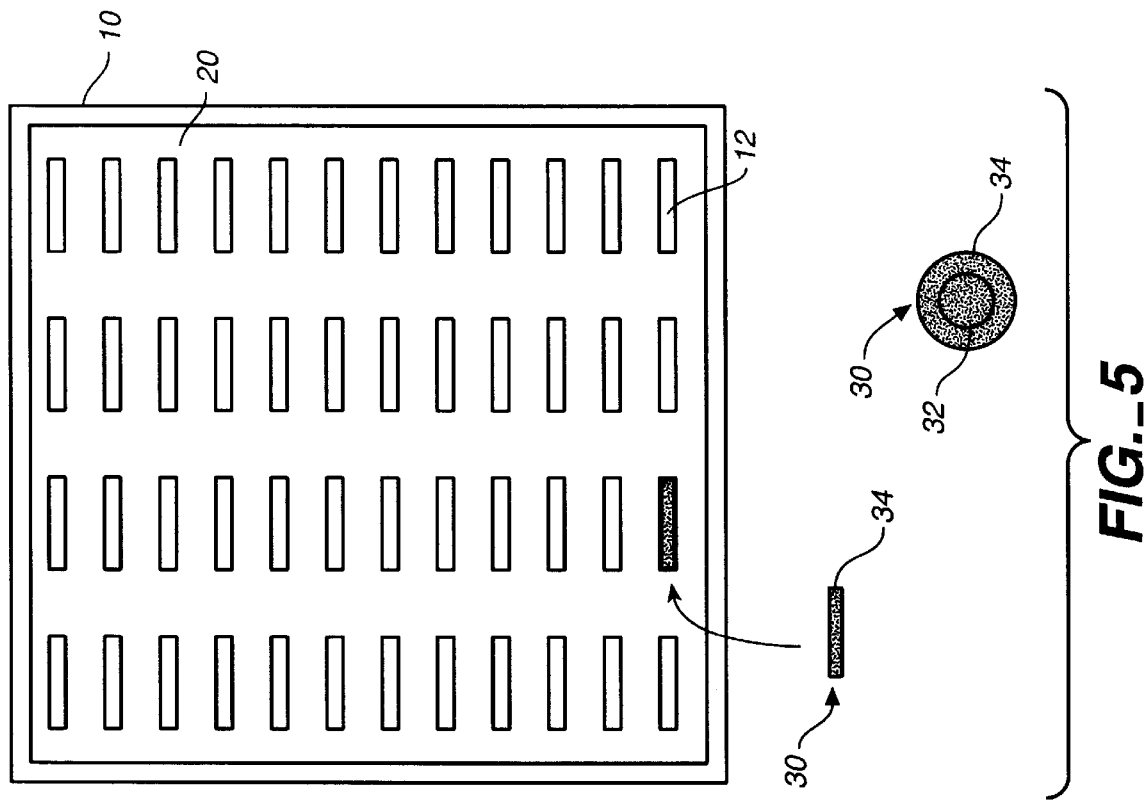
FIG._4
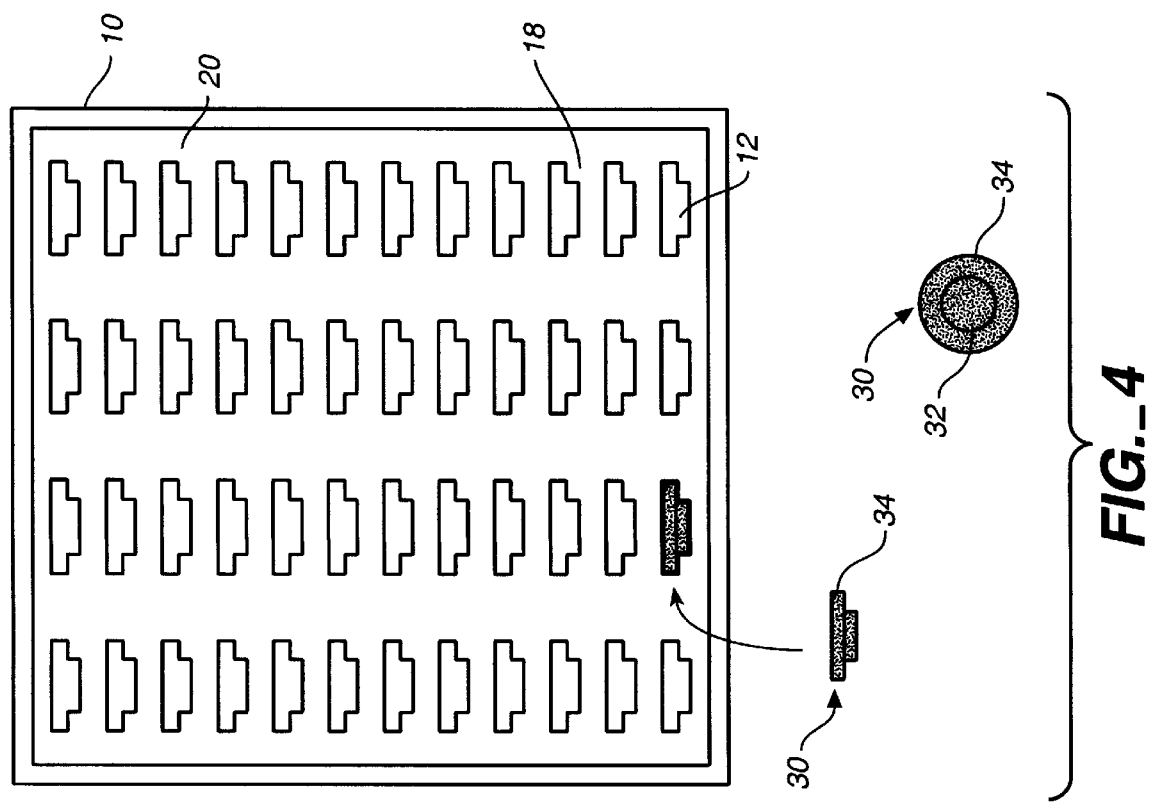
FIG._5

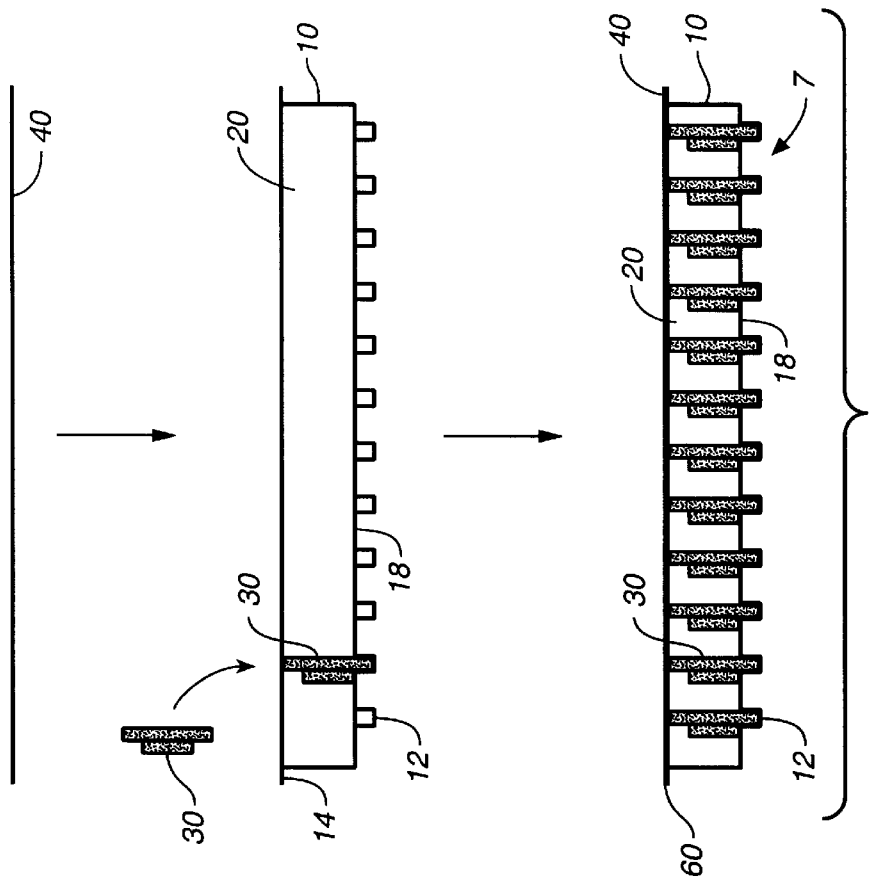
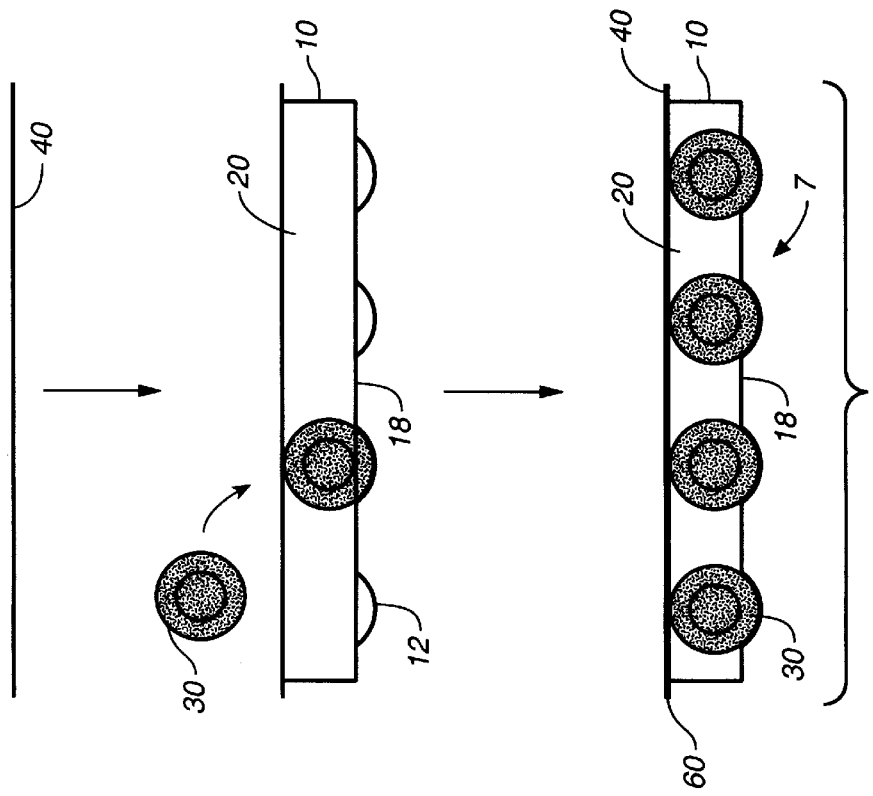

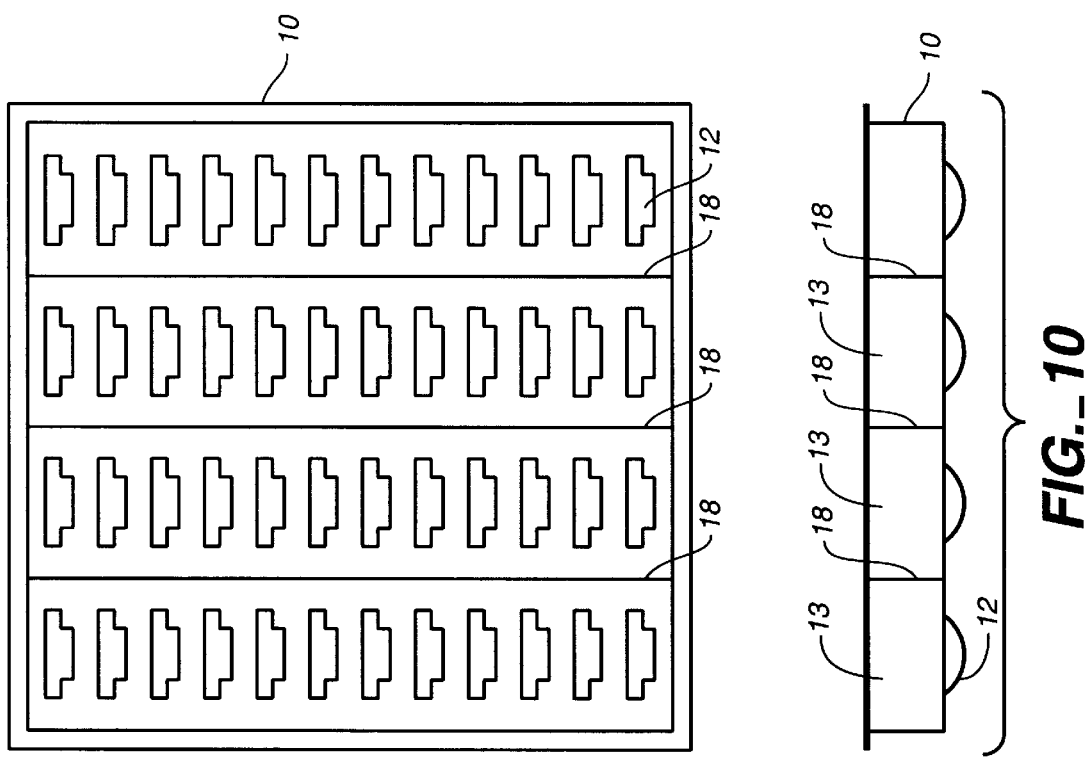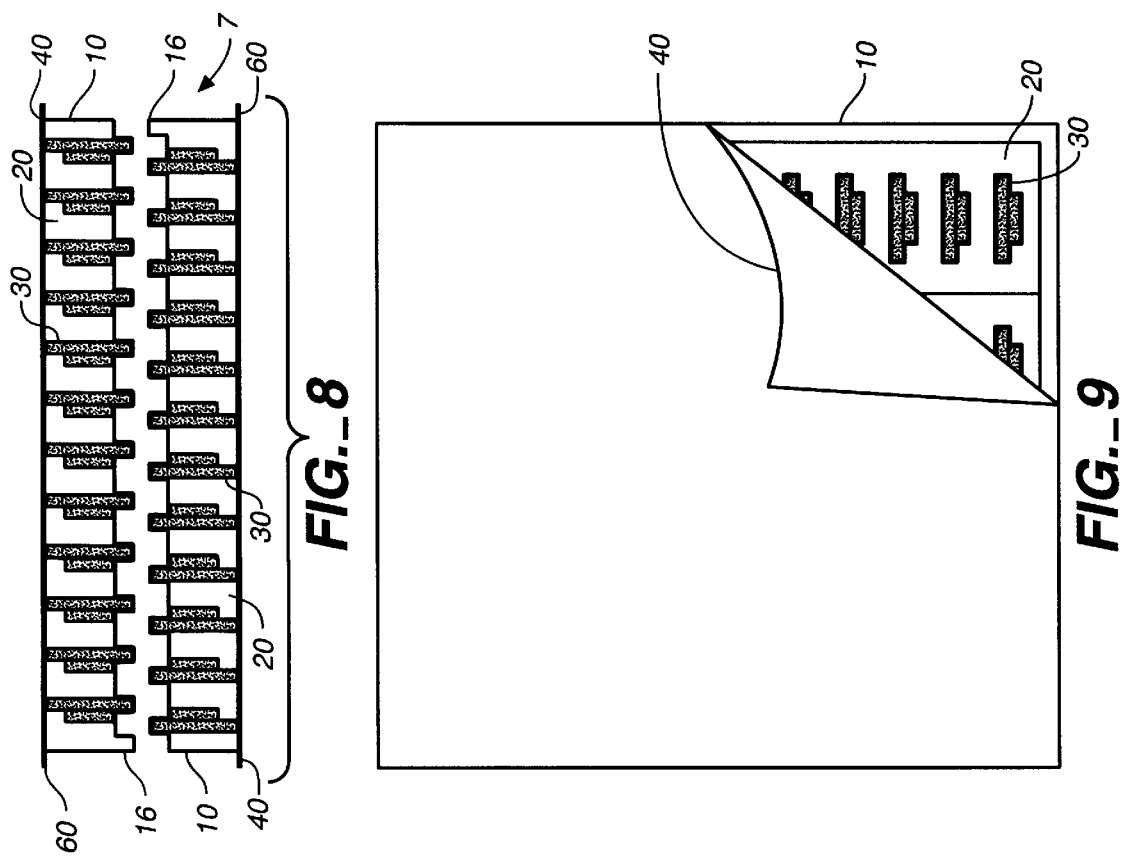

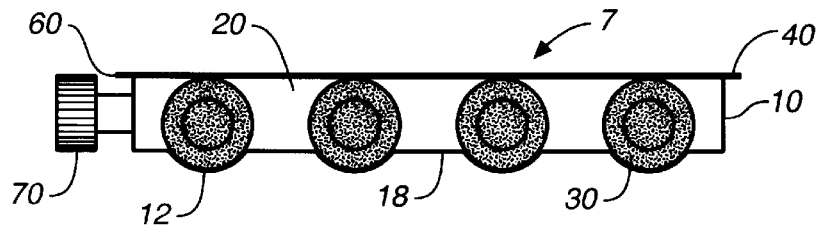
FIG._11
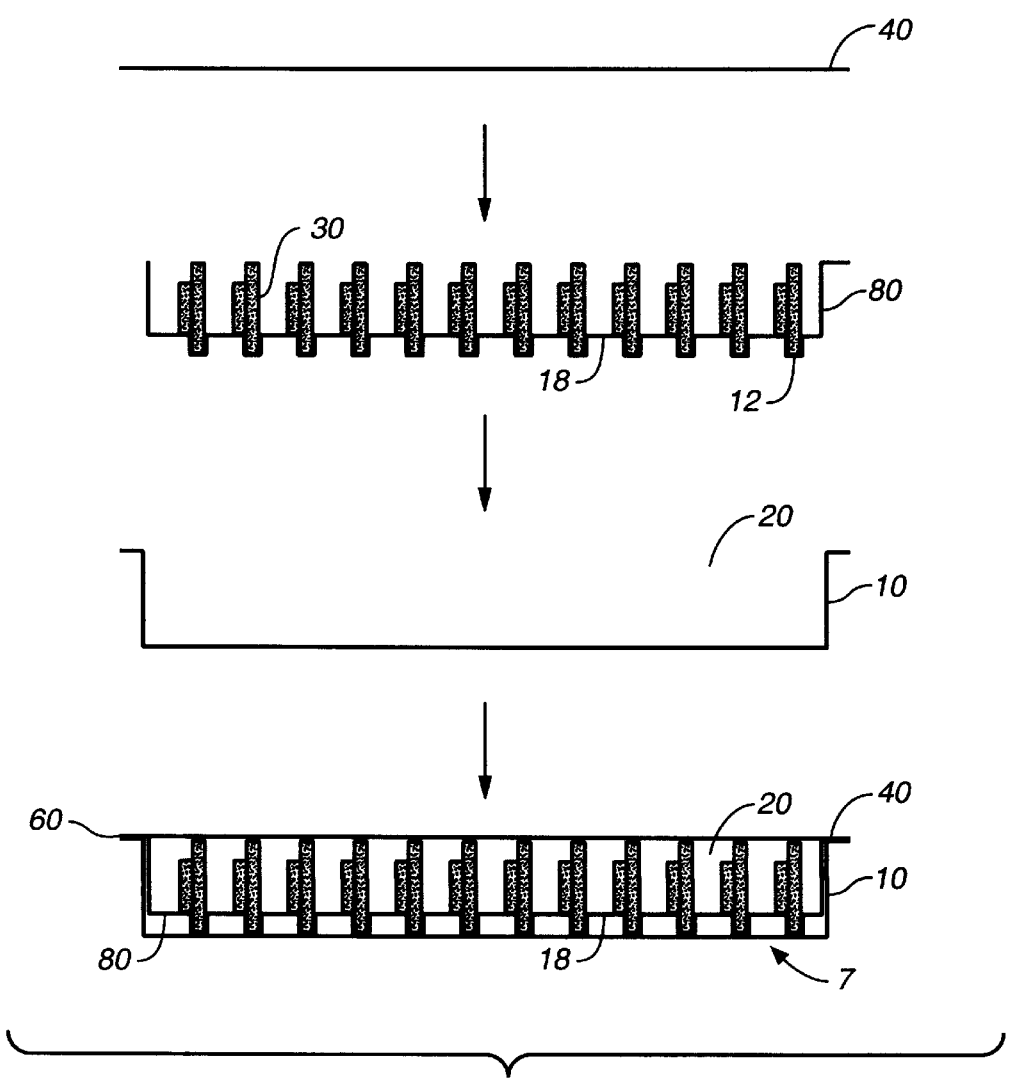
FIG._12

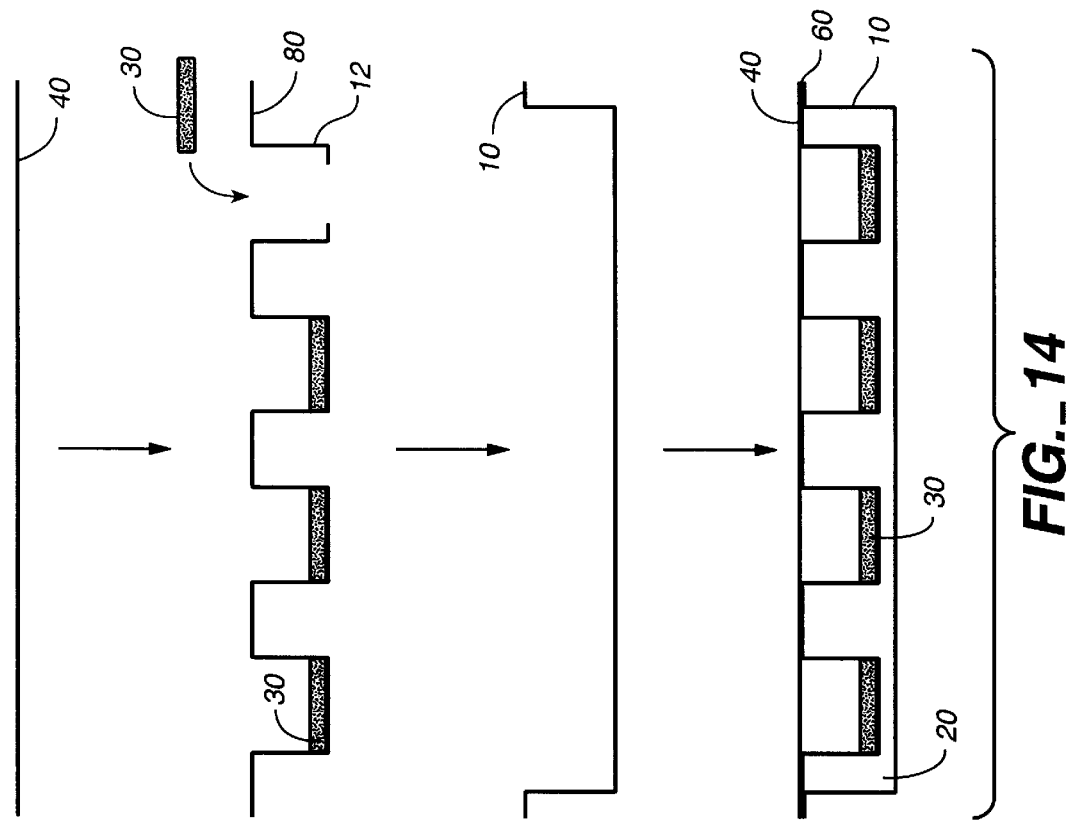
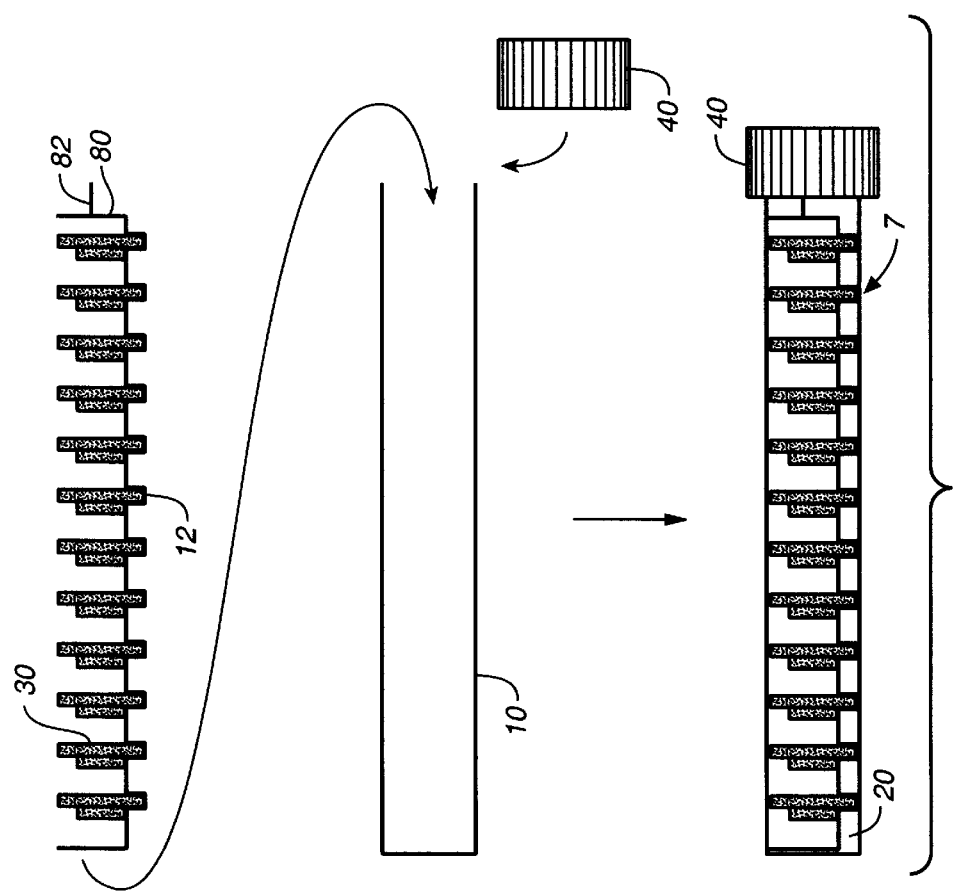

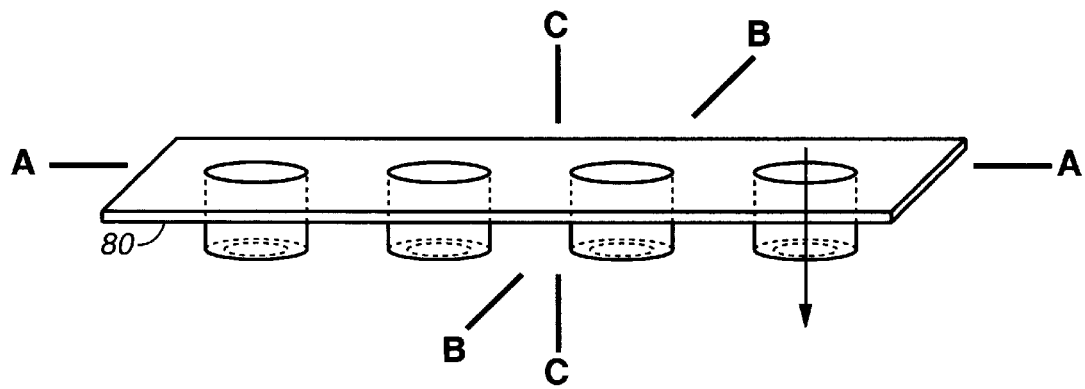
FIG._15
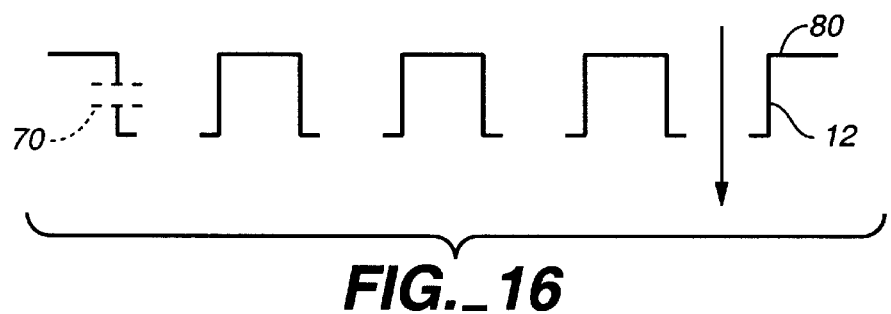
FIG._16
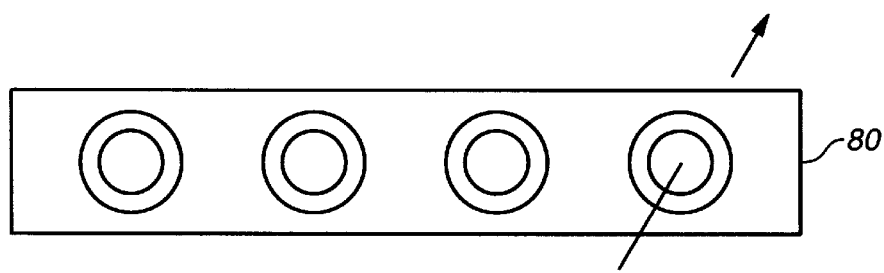
FIG._17
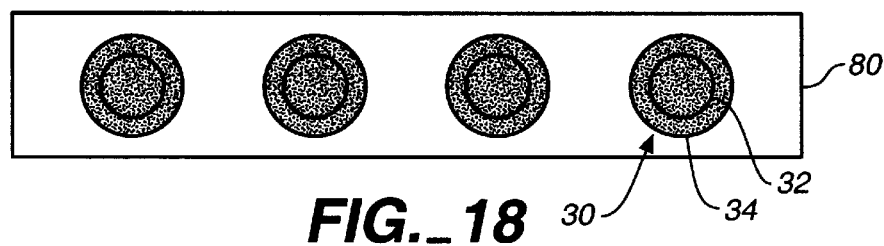
FIG._18

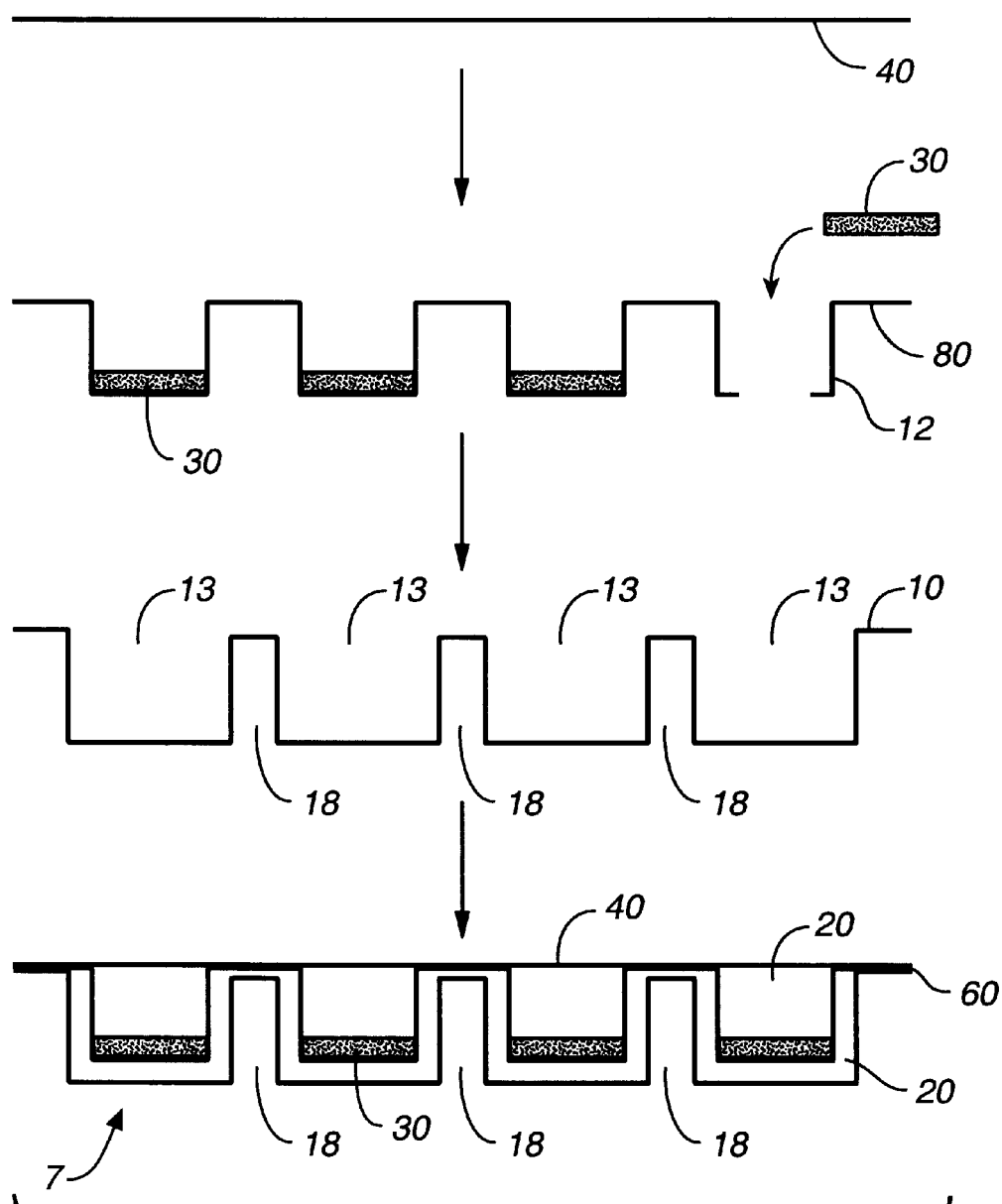
FIG._19

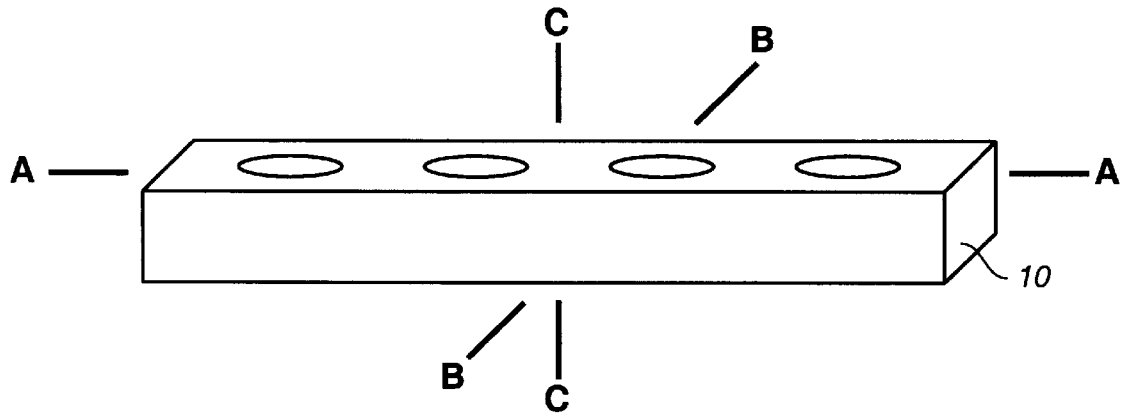
FIG._20
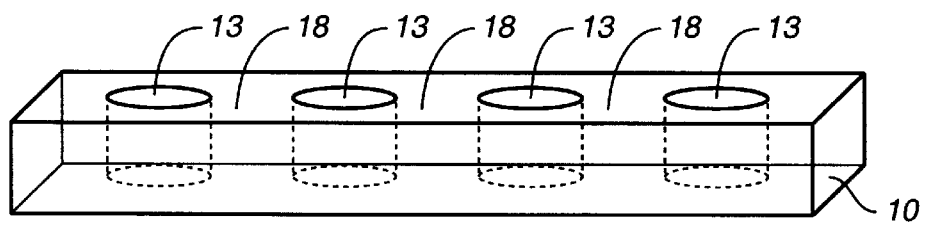
FIG._21
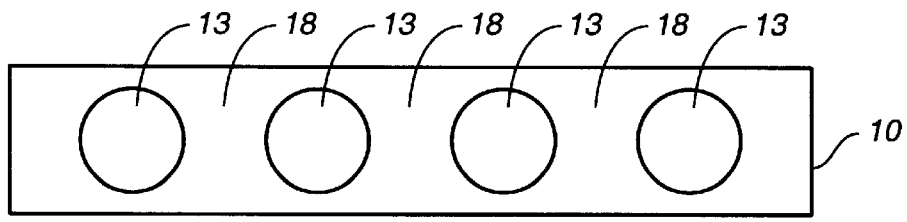
FIG._22

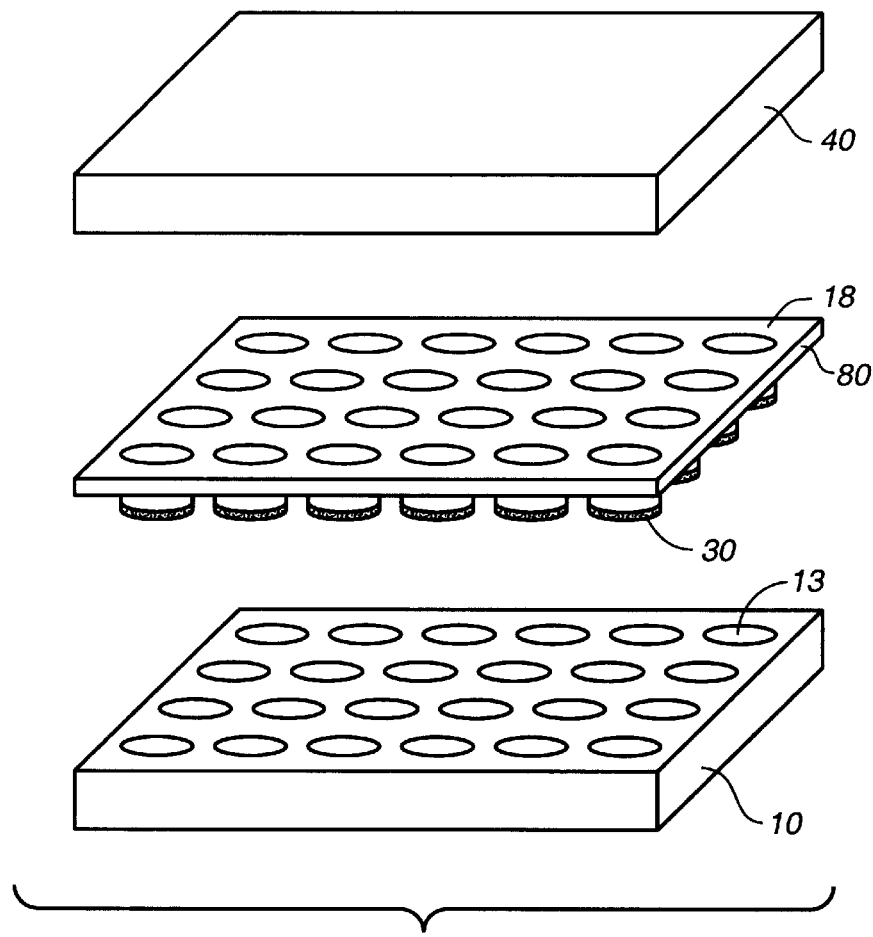
FIG._23
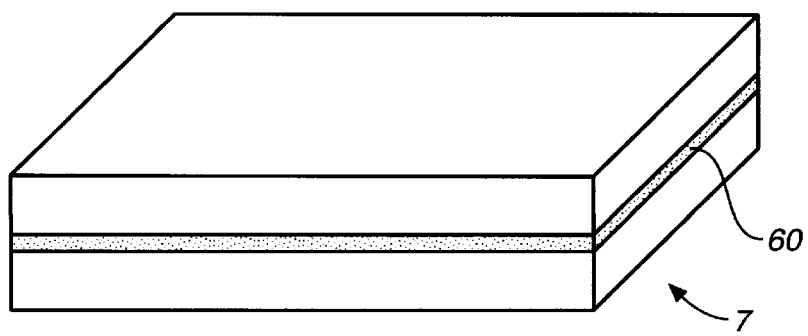
FIG._24

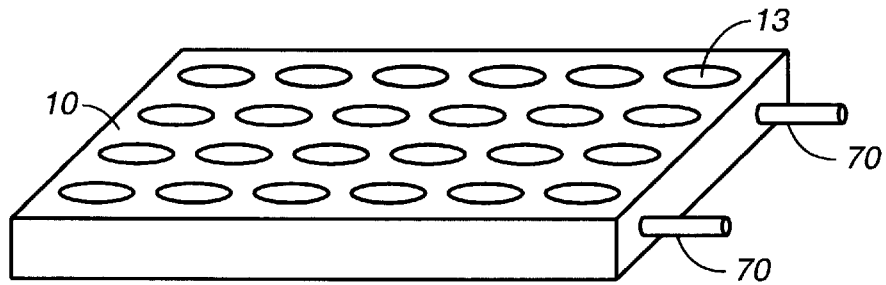
FIG._25
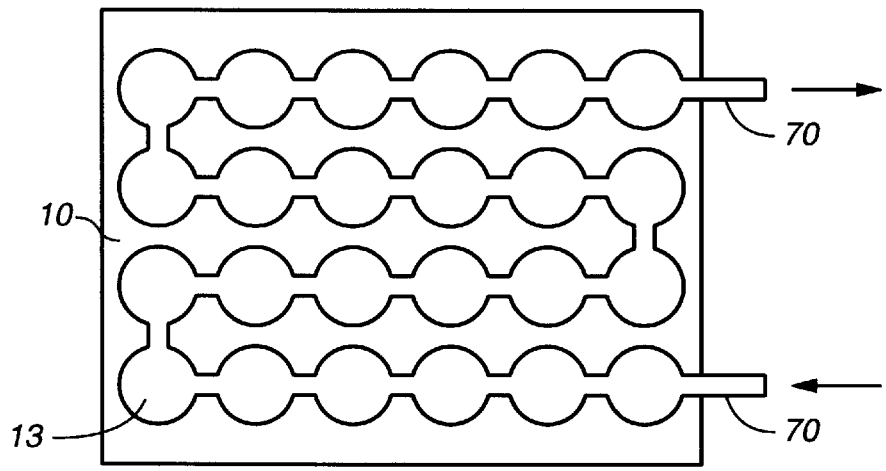
FIG._26
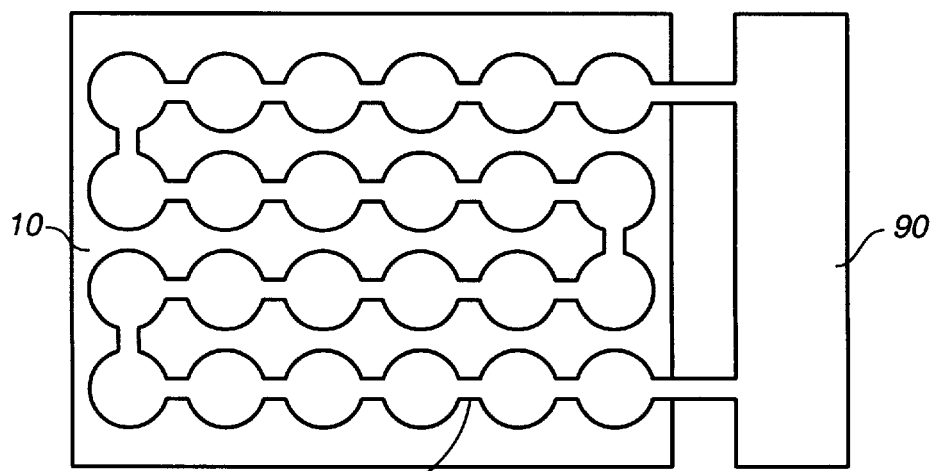
FIG._27

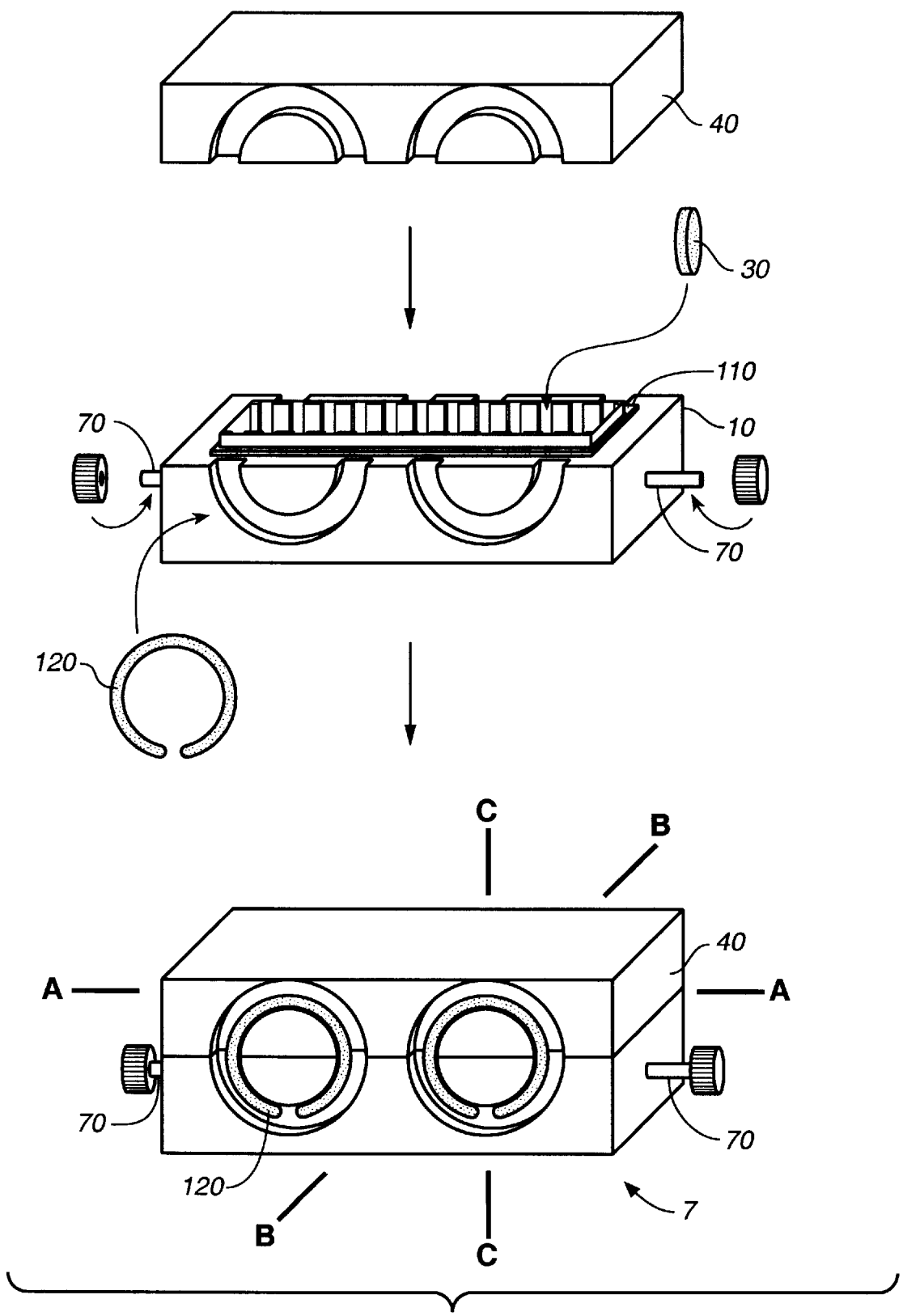
FIG._28

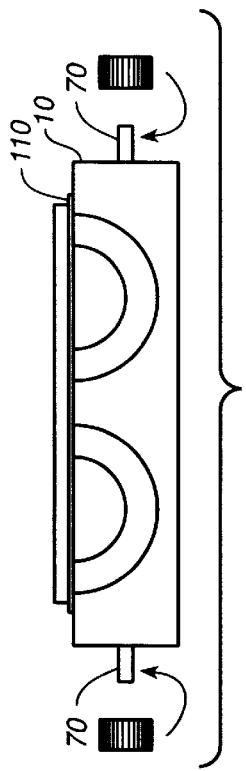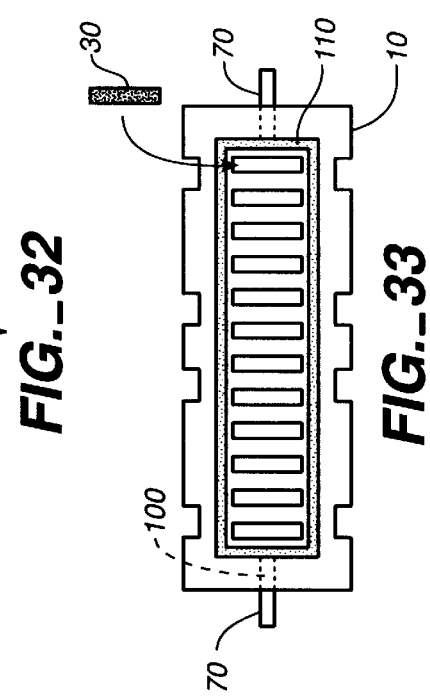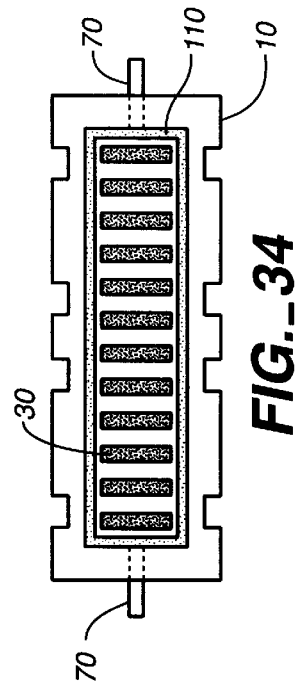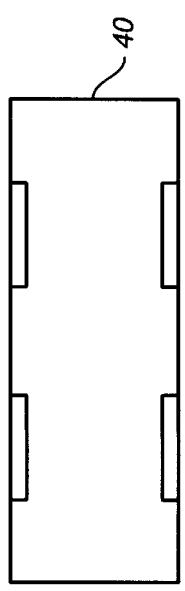

PACKING DEVICE FOR TRANSPORTING CONFLUENT CELL MONOLAYERS

CROSS REFERENCE TO RELATED APPLICATIONS

This application is related to U.S. Provisional Application Ser. No. 60/100,342 (Attorney Docket No.: NAVI-004/00US), filed Sep. 14, 1998.

FIELD OF INVENTION

The present invention relates to cell packaging and transport devices.

INTRODUCTION

Background:

Specialized cells utilized for scientific or industrial purposes are typically grown in sterile containers to a desired state of growth for a given experiment. In some cases the containers also are used to transport the cells from one location to the next. Unfortunately, cell cultures tend to lose viability and revert to a state of dormancy when the containers are removed from their original growth environment for any extended period of time. This is especially true for cells transported under variable conditions and distances, such as when ordered from a cell repository or commercial vender. As a result, cells that are ordered and shipped are typically packaged in a state of suspended preservation at the shipper's location as a storage inoculum, shipped and then re-cultured by the user upon arrival at the new location. This means that the user must not only spend the time and resources to re-culture the cells, it also results in significant delays while waiting for the cells to grow to a desired state of growth suitable for usage in an experiment.

These problems are further frustrated when the experiments require seeding and culturing of viable cell monolayers on permeable membranes, such as those requiring precision control over cell differentiation, density, and confluency. For experiments of this type, permeable membranes with cell monolayers attached thereto are prepared on site. This is necessary because of the highly delicate nature of the cell monolayer-membrane relationship. For example, mechanical forces experienced during movement sheer, tear and/or otherwise mechanically damage individual cells and their contact with each other, thus destroying confluency of the monolayer and rendering them useless. Additionally, any extended removal of the membrane-cell monolayer preparations from a relatively small temperature window results in altered cell growth and/or cell cycle.

Accordingly, it would be desirable to provide a method and device suitable for packaging and transporting confluent cell monolayers attached to permeable membranes that are ready-to-use upon delivery.

Relevant Literature:

U.S. Pat. No. 4,143,765 discloses a shipping and display tray for tissue culture dishes. U.S. Pat. No. 5,415,277 discloses stackable containers. U.S. Pat. No. 5,084,393 discloses a cell culture container lined with a plurality of bristle-shaped projections. U.S. Pat. No. 4,734,373 discloses a disposable cell culturing device.

SUMMARY

The present invention relates to a disposable or recyclable cell packaging and transport device for shipping ready-to-use confluent cell monolayers on permeable membranes. The transportable device comprises a liquid impervious housing filled with fluid cell medium having reversibly disposed therein a plurality of spatially separated membrane inserts each having a viable confluent cell monolayer attached thereto, where the fluid filled housing comprises a removable lid that provides access to the membrane inserts, and where the fluid filled housing is essentially devoid of air pockets capable of damaging the confluency of the cell monolayer. The housing can comprise one or more internal compartments separated by liquid permeable or liquid impervious dividers, where the fluid cell medium and one or more of the membrane inserts are disposed in one or more of the internal compartments. The housing also may include one or more valves for circulating fluid therein and well as for removing excess air that is capable of damaging the confluency of the cell monolayer. The device optionally includes a disposable or recyclable environmental control system for regulating chemical and/or physical conditions of during transport.

The invention also provides a method for producing the device. The method involves removing air pockets from a liquid impervious housing that is filled with fluid cell medium and that is sealable by a removable lid, where the housing has disposed therein a plurality of detachable and spatially separated permeable membrane inserts each having a confluent cell monolayer attached thereon, and sealing the housing.

The device of the invention is configured to protect cells from mechanical injury so that assays or other experiments requiring even growth and specific cell densities can be performed upon delivery with minimal preparation and delays. The device of the invention also is readily adaptable for transporting cell monolayers normalized to any desired stage of cell cycle and/or growth, without the need to recalibrate cell cycle or synchronize growth upon receipt. The device is versatile, simple, light and compact, and can be used for transporting multiple different types of cell monolayers on a variety of permeable membranes.

BRIEF DESCRIPTION OF FIGURES

FIG. 1 shows the constituent parts of the device according to the invention.

FIG. 2 shows the device of FIG. 1 assembled.

FIG. 3 shows the device of FIG. 2 assembled with a temperature regulator.

FIG. 4 shows the interior of the housing base of the device of FIG. 2.

FIG. 5 shows alternative interior of the housing base of the device of FIG. 2.

FIG. 6 shows a side view of the housing along line A—A of FIG. 2.

FIG. 7 shows a side view of the housing along line B—B of FIG. 2.

FIG. 8 shows two devices of FIG. 6 adapted for secure stacking.

FIG. 9 shows a top view of a peel away lid of the device of FIG. 2.

FIG. 10 shows the housing of FIG. 2 with compartments defined by extended dividers.

FIG. 11 shows an alternative device of FIG. 6 with a valve attached to a side wall of the housing.

FIG. 12 shows an alternative device of FIG. 7 with a detachable receptacle assembly.

FIG. 13 shows an alternative device of FIG. 7 with a detachable receptacle assembly.

FIG. 14 shows an alternative device of FIG. 7 with a detachable receptacle assembly.

FIG. 15 shows a detachable receptacle assembly of device of FIG. 14.

FIG. 16 shows side view of a detachable receptacle assembly of device of FIG. 15.

FIG. 17 shows a top view of a detachable receptacle assembly of device of FIG. 15 without membrane inserts.

FIG. 18 shows a top view of a detachable receptacle assembly of device of FIG. 15 with membrane inserts.

FIG. 19 shows an alternative device of FIG. 14 with a detachable receptacle assembly and internal compartments of assembled housing separated by dividers.

FIG. 20 shows housing base of FIG. 14 for receiving detachable receptacle assembly.

FIG. 21 shows transparent view of housing base of FIG. 20.

FIG. 22 shows a top view housing base of FIG. 21.

FIG. 23 shows an alternative device of FIG. 7 with a detachable receptacle assembly and lid.

FIG. 24 shows device of FIG. 23 assembled.

FIG. 25 shows housing base of device of FIG. 24 with valves.

FIG. 26 shows top view of housing base of FIG. 25 with fluid channels.

FIG. 27 shows top view of housing base of FIG. 26 with fluid circulator.

FIG. 28 shows alternative device of FIG. 11.

FIG. 29 shows side view of lid of device of FIG. 28.

FIG. 30 shows top view of lid of device of FIG. 28.

FIG. 31 shows bottom view of lid of device of FIG. 28.

FIG. 32 shows side view of housing base of device of FIG. 28.

FIG. 33 shows top view of housing base of device of FIG. 28 without membrane inserts.

FIG. 34 shows top view of lid of device of FIG. 28 with membrane inserts.

Drawing Reference Numerals:

7 constituent parts of cell packaging and transport device
10 housing base
12 receptacle for holding membrane insert
13 compartment
14 housing base flange for forming seal with lid
16 lock for stacking devices
18 divider for separating receptacles
20 fluid cell medium
30 membrane insert
32 confluent cell monolayer on permeable membrane
34 permeable membrane support
40 lid for sealing housing base
50 temperature regulator
60 seal formed between housing base and lid
70 valve for controlling fluid or air flow
80 detachable receptacle assembly for holding membrane inserts
82 handle
90 fluid circulator
100 fluid channel
110 gasket
120 clamp

DESCRIPTION OF SPECIFIC EMBODIMENTS

A disposable or recyclable device is provided for packaging and transporting viable confluent cell monolayers on permeable membranes that are ready-to-use upon delivery. The transportable device of the invention comprises a fluid impervious housing having four basic components: (i) a housing base for receiving fluid; (ii) fluid cell medium disposed in the housing base; (iii) a plurality of spatially addressable and separated membrane inserts each having a confluent cell monolayer attached thereto; and (iv) a removable lid for reversibly sealing the housing base so that the fluid cell medium and membrane inserts are separated from an external environment and the sealed housing is essentially devoid of air pockets capable of damaging the confluency of the cell monolayer.

The housing base is formed by fluid impermeable bottom wall and side wall. One or more bottom and side walls define an interior of the housing base which is capable of retaining fluid. The side wall terminates in an opening sized for receiving one or more detachable membrane inserts. The interior of the housing contains a plurality of spatially separated receptacles configured for detachably receiving the membrane inserts in a spatially addressable array within the housing base. The receptacles can be formed by one or more walls of the housing base or provided as part of a separate detachable membrane insert assembly that is received within in the interior of the housing. The membrane inserts include a permeable membrane upon which a confluent monolayer of cells is attached thereon. The confluent cell monolayer consists essentially of a single layer of cells that are in contact with each other. The cells may be provided on one or both sides of a surface of a membrane of comprising the insert, to provide multi-cell configurations. Mixed cultures may be represented as well. The permeable membrane of the insert is composed of a material that permits selective passage of a substance, such as a fluid, cell nutrients, ions, etc. may represent a semi-permeable membrane, microporous membrane and the like, and has a surface area suitable for supporting a viable confluent cell monolayer thereon. The fluid cell medium is disposed in an interior of the housing base. The fluid cell medium is preferably a liquid, and can be any cell growth medium or preservation medium that maintains viability of the cell monolayers following packaging and during transport of the assembled device. The opening of the housing base is reversibly sealable by a fluid impermeable lid. The lid is utilized to directly or indirectly form an airtight seal with the housing base so as to provide the fluid cell medium filled liquid impervious housing containing the plurality of membrane inserts with cell monolayers.

When the device of the invention is assembled, an interior of the housing base is filled with the fluid cell medium and is essentially devoid of air pockets (air or any other "air pocket" forming gas) that are capable of disrupting the integrity of the cell monolayer during transport. The membrane inserts are disposed in the fluid filled interior of the housing base, and the cell monolayers of the inserts are completely enveloped by the fluid cell medium. The membrane inserts are spatially separated and held in place in the assembled housing by the receptacles. The receptacles are separated by dividers, which define the spatial arrangement of the receptacles. An airtight seal is provided indirectly or directly between the fluid filled housing base and the lid so as to separate the inserts from an external environment and to prohibit formation of air pockets in the fluid filled interior of the housing during transport.

The device of the invention protects the cell monolayers from mechanical injury during transport by providing a transport environment in which the monolayers are enveloped by a protective fluid cell medium in the substantial absence of excess air pockets. By excluding excess air, the device protects the integrity of the cell monolayer by providing a fluid filled housing interior devoid of cell monolayer damaging air pockets, or excess air that would otherwise be capable of forming damaging air pockets such as unwanted bubbles of air during prolonged transport. Exclusion of excess air therefore protects the cells from mechanical injury and fluid shear stresses that would otherwise arise from sloshing media and the like.

The device of the invention optionally includes a disposable or recyclable environmental control system for regulating chemical and/or physical conditions during transport. The environmental control system includes a disposable or recyclable temperature regulator for maintaining a desired temperature of the fluid cell medium during transport. This permits transport of the device under conditions where temperatures can vary beyond a suitable range that would otherwise alter cell growth or differentiation. The environmental control system may also represent a disposable or recyclable fluid circulator for circulating a fluid through an interior of the housing base. This permits a fresh or recirculated supply of fluid cell medium to be provided to the cell monolayers, as well as maintaining the interior of the assembled fluid impervious housing substantially free of cell monolayer damaging air pockets. The fluid circulator also may be utilized to purge the interior of the assembled housing of air pockets prior to sealing and/or during transport. The device also may comprise a multi-compartment configuration, where a compartment is separated by a divider that forms a seal with the lid. The divider is preferably provided by a wall of the housing base. One or more fluid permeable or impermeable dividers can be included to separate compartments.

The compartments may define a plurality of spatially separated and addressable interior compartments, or receptacles, suitably configured for receiving the plurality of membrane inserts, or a detachable receptacle assembly, such as a multi-well configuration.

FIG. 1 shows the constituent parts of the cell packaging and transport device 7 of the invention. FIG. 2 shows device 7 assembled. The preferred embodiment depicted in FIG. 1 comprises a housing base 10 that provides a plurality of receptacles 12 formed by the bottom and side walls of the base. The receptacles are provided within an interior of the housing base and are separated by dividers 18. The receptacles are configured for detachably receiving membrane inserts 30 within the housing base. The housing base, when sealed with a lid 40, contains fluid cell medium 20 that completely envelops the cell monolayers in the absence of air pockets capable of damaging the integrity of the cell monolayer when the device of the invention is transported. Thus, the assembled device 7 provides a fluid filled housing interior devoid of cell monolayer damaging air pockets.

Materials employed for construction of the housing and lid are any liquid and gas impervious materials compatible for maintaining cell viability. The materials may be natural, synthetic, or composites thereof. They include, but are not limited to, natural and synthetic polymers, synthetic rubbers, elastomers, and plastic and thermoplastic materials. The material selected is compatible with maintaining the viability of the cell monolayer. In one embodiment, the housing base is made of a more rigid plastic, and the lid is made of a softer, yielding plastic disposed over the opening of the housing base and secured thereto by various reversibly adhesive approaches including glues, heat sealing, crimping and the like. This permits the device of the invention to be arranged in a preferred "peel away" configuration, i.e., a peel away lid, as depicted in FIG. 9. In an alternative embodiment, the housing base and lid are provided as rigid material components. This aspect of the invention is illustrated in FIG. 28.

The housing base 10 of the device according to the present invention may advantageously be formed by blow-forming from a suitable thermoplastic material. Blowforming includes blow-extrusion forming, in which a thermoplastic material is extruded and a pressurized fluid introduced in its interior, typically an air "bubble" whose pressure and flow rate determines the dimensional characteristics of the blown material. Blow forming also includes blow-molding, in which heated thermoplastic material is passed into an enclosing mold where a pressurized gas expands the material as a film into contact with the interior surfaces of the mold. The housing base also may be vacuum-formed using polymers suitable for this purpose and various techniques known in the art. The housing base also may be formed by machining of solid materials. The lid 40, receptacle 12, compartment 13, and detachable receptacle assembly 80, as well as other constituent parts of the device of the invention also may be formed by these methods.

FIGS. 4 and 5 show a top view of the housing base 10 of FIG. 1. The receptacles 12 are separated by dividers 18 and are configured and spatially arranged for receiving a plurality of detachable membrane inserts 30. The detachable membrane insert of the device includes a permeable membrane 32 upon which a confluent monolayer of cells is attached. The permeable membrane of the insert is composed of a permeable membrane material and has a surface area suitable for supporting a viable confluent cell monolayer thereon. The permeable membrane may be provided in a support 34 that holds the membrane in place, such as a frame or scaffold assembly, or layered on various microporous substrata capable of supporting the membrane in a substantially uniform and rigid configuration. Alternatively, the permeable membrane itself may be composed of a self-supporting material. The membrane insert may be reversibly or irreversibly received by a receptacle, such as when provided as a detachable receptacle assembly 80 illustrated in FIG. 23.

The permeable membrane 32 which the confluent cell monolayer is provided may be formed of any material capable of supporting viable cells, while allowing at least selected materials to pass through and contact the cells. Such materials include microporous membranes, hydrated gels, ultrafiltration membranes, or layered combinations such as a gel supported on a screen. The permeable membranes may be provided with various pore sizes, textures, and the like, and can be composed of different types of permeable materials, or materials into which pores can be introduced. Examples of suitable materials include, but are not limited to, polycarbonate, polyester, porcelain, cellulose, nitrocellulose, nylon and the like.

The membrane inserts 30 are configured for easy insertion and removal from the housing base 10 of the device. For instance, they may be configured so as to be received by receptacles 12 formed by one or more walls of the housing base, or for insertion into a detachable rack or sleeve assembly 80 that can be placed and removed from the housing base. Thus the membrane inserts can have any of a number of geometrical shapes, and may be multidimensional. The membrane inserts also can include one or more flanges, apertures, folds, handles and the like depending on its intended end use. The membrane inserts preferably include one or more handles, flanges or apertures, or combinations thereof, for facilitating insertion and detachment from the housing base of the device. In a preferred embodiment, the membrane inserts are configured so as to permit their easy application in an apparatus that utilizes at least the insert's membrane as part of an experiment requiring a permeable membrane having a cell monolayer thereon. Preferred configurations of the membrane inserts have a generally flat permeable membrane surface area. The membrane inserts can be designed and fabricated de novo, or obtained from various commercial venders. Suitable membrane inserts for use in the device of the invention include those described in U.S. Pat. Nos. 5,759,851; 5,139,951; 5,272,083; and U.S. Pat. No. 4,142,940.

FIG. 4 shows a housing base having a receptacle design for receiving a multidimensional membrane insert having a "hat" configuration. FIG. 5 shows a housing base having an alternative receptacle design for receiving and holding a generally flat membrane insert. FIG. 6 depicts a transparent side view of the device of FIG. 1. Receptacle 12 provides at least one groove with side walls into which a permeable membrane support 34 fits and is removably held. When the detachable membrane insert 30 is received in the receptacle, the confluent cell monolayer on permeable membrane 32 is capable of contacting fluid cell medium 20 only. The groove and side walls of the receptacle can be provided by any structure that holds the membrane insert in place within an interior of the housing base and limits contact of the permeable membrane insert with the confluent cell monolayer to the fluid cell medium. A preferred receptacle provides opposing parallel grooves formed by one or more walls of the housing base permitting an edge portion of the permeable membrane support 34 to fit in each groove so that, when the membrane insert is placed in the receptacle, it is removably held within the housing base. FIG. 12 shows an alternative device depicted in FIGS. 6 and 7 that has a detachable receptacle assembly 80 for insertion into a housing base 10.

FIGS. 6 and 7 also depict unassembled and assembled device 7 of FIG. 1, with seal 60 formed between lid 40 and housing base 10. In a preferred embodiment, flange 14 is provided by the housing base that contacts and forms a seal with the lid. The seal is formed by any means that is compatible with maintaining cell viability. This includes heat sealing, solvent bonding, ultrasonic welding, clamping, taping, complementary threading provided by the housing base and lid, and the like. A gasket 110, such as depicted in the device of FIG. 28, also may be utilized in forming a seal between the housing base and lid. The housing base is sealed in a manner such that the fluid filled housing is devoid of monolayer damaging air pockets and the cell monolayers on the membrane inserts are completely enveloped by the fluid medium to minimize abrupt fluid movement during transport. This may advantageously be accomplished by utilization of one or more valves that are capable of removing excess air or other gas from a fluid filled housing interior. The valve halts or controls flow of fluid or air, and includes one-way or two-way flow valves.

The valves may be formed by a sealable opening between the housing base 10 and lid 40, or connected to a wall of the housing base or the lid, and in fluid communication with housing interior, or any combination thereof. For instance, when the valve is formed by a sealable opening between the lid and the housing base, and the base or lid is formed of a flexible material, excess air can be removed by simply squeezing the fluid filled base/lid and then sealing the opening. Examples of other valves include filling ports or bleed ports attached to a wall of the housing base that are utilized to add fluid to the assembled housing and/or to remove excess air after sealing with the lid. FIG. 11 depicts a side view of an alternative device of the invention depicted in FIG. 6 that includes valve 70 for filling the housing base with fluid cell medium 20, or for removing excess air from the housing base that would otherwise be capable of forming air pockets, that could damage the integrity of the cell monolayers during transport.

It is preferred that at least the bottom wall of the housing base is configured for secured stacking with at least one other device of the invention. This may advantageously be accomplished by including at least one stacking lock 16 on the exterior of the housing base 10 that is received by a complementary stacking lock 16 provided a second housing base 10 as illustrated in FIG. 8. The lid of a first device 7 also may provide a stacking lock, or provide a recess or impression therein into which the bottom of a housing base 10 of a second device 7 fits. Of course any of stacking means can be employed, such as those described in U.S. Pat. No. 5,415,277.

FIG. 10 depicts an alternative embodiment of the device depicted in FIG. 1 for providing separate compartments within the housing base 10. Divider 18 that forms a seal with the lid 40 defines a compartment 13. A divider can be permeable or impermeable to a substance of interest. When a divider of the device depicted in FIG. 10 is impermeable to the fluid cell medium, different types of fluid cell medium can be provided in each compartment. This permits simultaneous packaging and shipping of different cell types in the same housing base, or cells of the same type to be provided in different mediums for variable growth, differentiation and the like. FIG. 19 also depicts an alternative embodiment of the device shown in FIG. 1 for providing separate compartments 13 within the housing base 10. In this embodiment, membrane insert 30 is reversibly or irreversibly received by receptacle 12. Receptacle 12 has an aperture substantially perpendicular to a side wall of receptacle 12 so as to permit fluid permeable contact of the horizontally received membrane insert with fluid cell medium 20 when the device 7 is assembled. FIG. 23 depicts an embodiment of FIG. 19 for providing separate compartments 13 within the housing base 10. Detachable receptacle assembly 80 provides a plurality of receptacles 12 having a plurality of membrane inserts 30, where assembly 80 is configured for reversible mounting by housing base 10, as depicted in FIG. 24. Compartment 13 receives the receptacles within its interior, the device is assembled and the compartments, each having a single membrane insert disposed therein, are completely filled with fluid cell medium and sealed by lid 40. FIG. 24 also depicts an alternate seal 60 capable of being formed between lid 40 and housing base 10. In this illustration, the seal is a sealant strip, such as an adhesive tape.

The permeable membrane 32 of a membrane insert 30 may be treated to produce a variety of surfaces for modulating cell attachment. For example, the treatment can be selected so as to promote or deter attachment of a particular cell type, as well as modulating attachment of cells of the same type but at different stages of growth or differentiation. Treatments suitable for this purpose may be physical, chemical, biological, or combinations thereof. Various physical, chemical and biological treatments suitable for this purpose are well known. Physical treatments include corona discharge plasma treatments which make polymer surfaces such as polycarbonate more hydrophilis for improved cell attachment. Chemical treatments include agents that alter hydrophilicity of the membrane surface or cellcell interactions (e.g., buffers, salts, solvents etc.). Biological treatments include agents that relate to ligand-receptor binding interactions, such as lipids, carbohydrates and proteins (e.g., antibodies, antibody fragments, integrins, extracellular matrix proteins and carbohydrates constituents and the like).

The permeable membrane 32 also can be divided into regions, where a different cell type is provided in a different region. This can be accomplished by treating each region with a different compound to produce multiple different cell attachment surfaces so as to attract a particular cell type to a given region of choice. In an alternative embodiment of the invention, the permeable membrane may be provided as a sheet that is disposed within the interior of the liquid impervious housing. The sheet is divided into regions onto which cell monolayers are attached. These regions may be suitably formed by dividers 18 provided by housing base 10, and/or housing base and lid 40.

Any cells capable of being applied as or forming a confluent monolayer on a permeable membrane can be utilized in the invention. Examples are endothelial, epithelial, adenocarcinoma, lymphocytes, sarcoma, fibroblasts, kidney, glial cells and co-cultures thereof. Preferred cells are endothelial and epithelial cells capable of polarization, where polarization refers to formation of apical and basolateral surfaces. Of particular interest are mucosal cells that include, but are not limited to intestinal, buccal, vaginal and lung cells. Examples of epithelial cells include euterocytes, hepatocytes and mixtures of cells (co-cultures). Examples of preferred cells include Caco-2, HT-29, T84, C2Bbe, MDCK, HeLa and CHO cells. Also, endothelial cells of interest include blood-brain barrier cells, such as bovine and human brain microvessel endothelial cells.

The permeable membrane insert 32 with cell monolayer thereon can be prepared using any number of methods. This includes seeding the permeable membrane with cells at an appropriate cell density and allowing a cell monolayer to form. In general, the conditions under which the cells are prepared relate to the cell type used. The cells also can reside on one or both sides of the membrane depending on the intended end use.

Cells can be seeded at known densities onto the membrane inserts. The membranes can be treated to promote cell attachment and growth. If differentiated cells are required, the fluid medium can be supplemented with growth regulators following standard techniques known in the art. The membrane inserts can then be utilized for packaging and transport in the device of the invention. In a preferred embodiment, Caco-2 cells are grown using Dulbecco's Modified Eagle's Media (DMEM) supplemented with 10% Fetal Bovine Serum, 5% Penicillin (5,000 units/ml)/Streptomycin (5,000 mg/ml), and 1% Non-essential amino acids under 95–100% humidity and 5% $CO_2$ at 37° C. Cells are grown in flasks and the culture split at 85–95% confluence. Membrane inserts are seeded at ~65,000 cells/cm$^2$ or a similar appropriate cell density and packaged in the device of the invention within 17–28 days post seeding to allow for differentiation.

The fluid cell medium 20 can be any fluid for growing or preserving the viability of cell monolayers. The fluid is preferably a liquid. The fluid cell medium is chosen for maintaining stability of a particular cell type, and preferably permits immediate usage of the cell monolayers in an assay of choice upon delivery of the device and removal of the seal with minimal preparation or washing. This includes buffer solutions and growth media, with or without preservatives. Examples of buffer solutions include but are not limited to, Hank's Buffer Solution (HBS); Ringer's Buffer Solution; and Phosphate Buffer Solution (PBS). Examples of medium include but are not limited to, Dulbecco's Modified Eagle Medium (DMEM); Minimum Essential Medium (MEM); BME Basal Medium; Insect Cell Culture Media; and Ham's F-12. Cell media can contain different concentrations of inorganic salts, sugars, amino acids, vitamins, and growth factors. The cell media also may be provided as a medium of increased nutrient concentration to lengthen the time between feedings.

The cell packaging and transport device optionally includes a temperature regulator that maintains the temperature of the local environment of the membrane insert during transport. The temperature regulator may include any portable heating/cooling unit capable of regulating the temperature of the fluid medium of the housing interior over a range that is compatible with maintaining viability of the cell monolayer, and may be disposable or recyclable. The heating/cooling unit regulates temperature preferably by electrical or chemical mechanisms. Of course the temperature window maintained by the temperature regulator depends on the particular cell type in question, and can be determined by one of ordinary skill in the art for a given type of cell. For instance, most mammalian cell monolayers maintain viability over temperature ranges of 20° C. to 45° C., and particularly 32° C. to 42° C. Thus, a temperature regulator selected for mammalian cells can be utilized to maintain these temperatures during transport.

The temperature window selected for transport of cells also may be set below optimal growth so as to reduce metabolism, thereby reducing utilization of nutrients. In this situation the user may incubate the cells upon receipt at a temperature to equilibrate them for a given experiment or other end use.

In a preferred embodiment, the temperature regulator is integrated with or removably attached to the cell monolayer packaging and transport device of the invention, as is illustrated by the temperature regulator 50 depicted in FIG. 3. When integrated with or removably attached to the cell monolayer packaging and transport device the invention, any temperature regulating unit (i.e., heating and/or cooling unit) can be utilized that is light, compact and capable of maintaining a temperature over a range that is suitable for maintaining viable cell monolayers. Examples include active or passive heating/cooling units. The preferred temperature regulator 50 is an electric cooler system for heating and cooling which provides a power source, a thermocouple device for accessing local temperature, and an electrically conductive coil attached to the power source. The conductive coil dissipates heat depending on the amount of current that passes through it.

The thermocouple controls the flow of power from the power source through the conductive coil to facilitate heating when supplied with current, or ambient cooling when the current is off. In general, the conductive coil is spatially arranged so that the coil dissipates the heat evenly. Other examples of temperature regulators that can be integrated with or attached to the device of the invention include various materials capable of retaining a particular temperature such as a gel slab, block, pack and the like.

The cell packaging and transport device also may be provided with a fluid circulator 90, as depicted in FIG. 27. In this embodiment, the fluid circulator is in fluid communication with the interior of the housing through valves 70. Fluid cell medium is pumped into individual compartments through fluid channel 100. The fluid circulator may contain a reservoir for collecting waste fluid medium, or it may simply provide a complete fluid circuit. A pumping device may be electrical, chemical or physical. Many such pumping devices are known. Provided a pump is compact, light, simple and reliable, does not incorporate air pockets in the fluid stream, and is capable of substantial sterilization, it may be utilized in the invention. The fluid circulator also may include a temperature regulator device. In this embodiment, temperature of the fluid circulated by the fluid circulator is maintained by a heating and/or cooling unit of the circulator.

As can be appreciated, the device and method of the invention allows shipment of ready-to-use confluent cell monolayers attached to permeable membranes. The cell monolayers are substantially free of mechanical damage, such as disrupted confluency by fissures, rips or gaps in cells, or altered cell growth and/or cell cycle. Thus, the user once receiving the packaged cell monolayers can perform assays or other experiments requiring even growth and dense cell populations upon delivery. The device of the invention also can be utilized for packaging and transporting multiple different types of cell monolayers on a variety of solid and permeable membrane substrata, the cells normalized to any desired stage of cell cycle and/or growth, without the need to recalibrate cell cycle or synchronize growth upon receipt. This permits a user to perform a desired experiment with minimal preparation and time delays. Perhaps more importantly, the invention also provides for a consistent source of viable cell monolayers that can be prepared under consistent and certified conditions by the shipper, which results in reproducible and reliable results.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A device for transporting viable confluent cell monolayers on permeable membranes, wherein said device comprises a liquid impervious housing having: a housing base defining an interior filled with fluid cell medium, a plurality of spatially addressable and separated membrane inserts each having a confluent cell monolayer attached thereon, and a removable lid, wherein said membrane inserts are disposed in said interior in a spatially addressable array, and said lid provides an air and liquid impermeable resealable seal with said housing base, and wherein said interior is substantially devoid of air pockets capable of disrupting the integrity of the cell monolayer during transport.

2. The device of claim 1, wherein said air pockets are air bubbles.

3. The device of claim 1, wherein said housing base is comprised of plastic.

4. The device of claim 1, wherein said removable lid is a peel away lid.

5. The device of claim 1, wherein said membrane inserts are received in a spatially addressable array of receptacles disposed in said interior.

6. The device of claim 5, wherein said detachable membrane inserts are removably received from said receptacles.

7. The device of claim 6, wherein said receptacles are formed by one or more walls of said housing base.

8. The device of claim 1, wherein said interior comprises a plurality of compartments.

9. The device of claim 8, wherein said compartments reversibly receive said receptacles.

10. The device of claim 1, wherein said device further comprises a temperature regulator.

11. The device of claim 1, wherein said device further comprises a fluid circulator.

12. The device of claim 1, wherein said fluid cell medium is liquid.

13. The device of claim 1, wherein said cell monolayer is comprised of one or more cells selected from the group consisting of Caco-2, HT-29, T84, C2Bbe, MDCK, HeLa and CHO cells.

14. The device of claim 1, wherein said cell monolayer is polarized.

15. The device of claim 14, wherein said cell monolayer is comprised of one or more of epithelial cells and endothelial cells.

16. The device of claim 15, wherein said epithelial cells are mucosal tissue cells.

17. The device of claim 16, wherein said mucosal tissue cells are intestinal cells.

18. The device of claim 15, wherein said endothelial cells are blood-brain barrier microvascular cells.

* * * * *